US00PP16603P2

(12) United States Plant Patent
Jonkers

(10) Patent No.: US PP16,603 P2
(45) Date of Patent: May 30, 2006

(54) ***IMPATIENS* PLANT NAMED 'FIFY REDTWO'**

(50) Latin Name: *Impatiens walleriana*
Varietal Denomination: Fify Redtwo

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 99 days.

(21) Appl. No.: 11/091,785

(22) Filed: Mar. 25, 2005

(51) Int. Cl.
*A01H 5/00* (2006.01)

(52) U.S. Cl. ..... Plt./317

(58) Field of Classification Search ..... Plt./317
See application file for complete search history.

*Primary Examiner*—Anne Marie Grunberg
(74) *Attorney, Agent, or Firm*—Jondle & Associates P.C.

(57) ABSTRACT

An *impatiens* cultivar particularly distinguished by its compact habit and red flowers is disclosed.

1 Drawing Sheet

Figure 1:
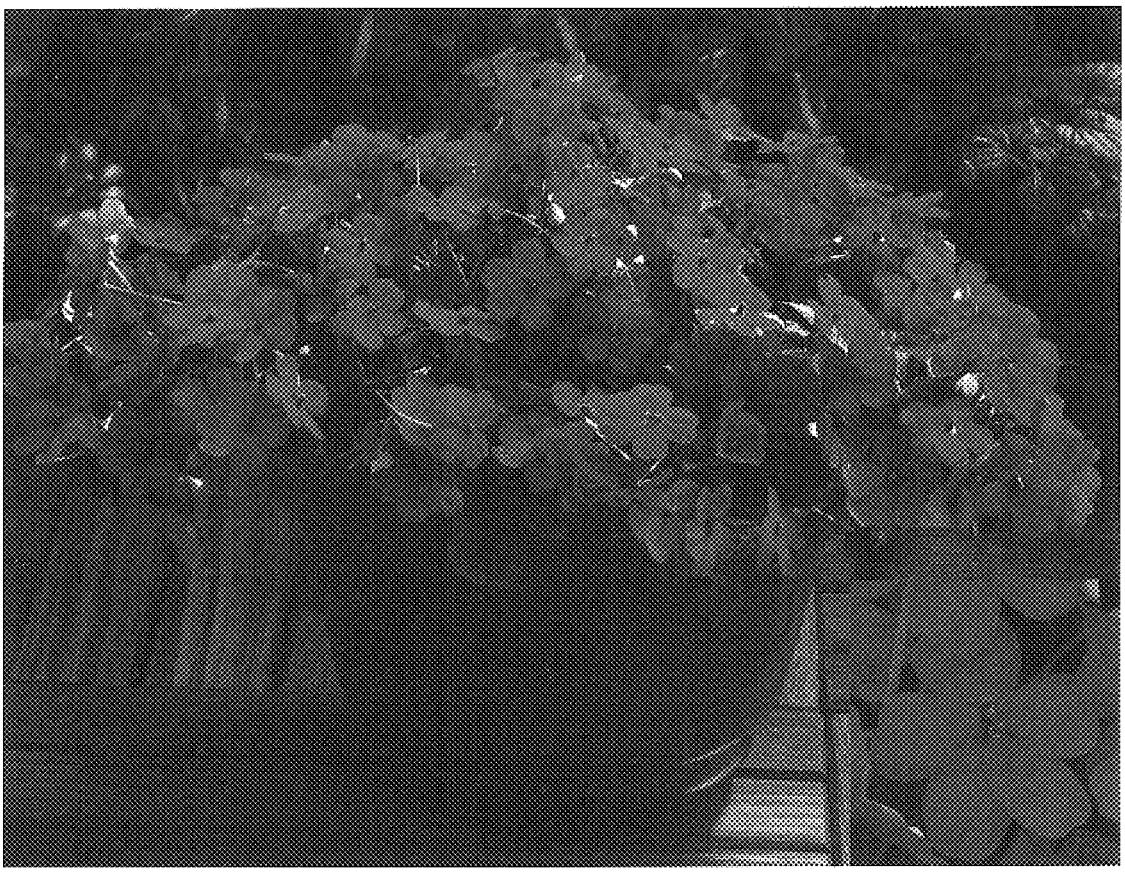

Genus and species: *Impatiens walleriana.*
Variety denomination: 'Fify Redtwo'.

BACKGROUND OF THE NEW PLANT

The present invention comprises a new and distinct cultivar of *impatiens,* botanically known as *Impatiens walleriana,* and hereinafter referred to by the cultivar name 'Fify Redtwo'. The new cultivar originated from a hybridization made in the year 2002 in Andijk, The Netherlands. The female parent was 'IMY-49-4', a red proprietary *impatiens* line (unpatented), while the male parent was 'IMY-54-2', a scarlet proprietary *impatiens* line (unpatented).

The new cultivar was created in 2002 in Andijk, The Netherlands and has been asexually reproduced repeatedly by vegetative cuttings and tissue culture in Gilroy, Calif. and Andijk, The Netherlands over a two-and-a-half-year period. The plant has also been trialed at Gilroy, Calif. and Andijk, The Netherlands. The present invention has been found to retain its distinctive characteristics through successive asexual propagations.

DESCRIPTION OF PHOTOGRAPH

This new *impatiens* plant is illustrated by the accompanying photograph which shows overall plant habit including blooms, buds, and foliage of the plant; the colors shown are as true as can be reasonably obtained by conventional photographic procedures.

FIG. 1. The photograph shows overall plant habit including blooms, buds and foliage; the inset shows the mature inflorescence.

DESCRIPTION OF THE NEW CULTIVAR

The following detailed descriptions set forth the distinctive characteristics of 'Fify Redtwo'. The data which defines these characteristics were collected from asexual reproductions carried out in Gilroy, Calif. The plant history was taken on five-month-old plants grown in one-gallon pots in a poly-covered greenhouse in the fall/winter season. Color readings were taken under natural light in the greenhouse in late winter. Color references are primarily to The R.H.S. Colour Chart of The Royal Horticultural Society of London (R.H.S.) (2001). Texture description details were observed with a dissecting microscope.

DETAILED BOTANICAL DESCRIPTION

Classification:
- *Botanical.*—*Impatiens walleriana.*
- *Common name.*—*Impatiens.*

Growth:
- *Form.*—Small, compact, mounded.
- *Growth and branching habit.*—Compact habit, good basal branching, moderately vigorous; pinching of the terminal apices enhances branching.
- *Height.*—5.0–10.0 cm as measured from soil level to top of plants.
- *Width.*—20.0–25.0 cm including flowers.
- *Time to produce a finished flowering plant.*—6–10 weeks for a 10-cm (4-inch) pot.
- *Outdoor plant performance.*—Shade; intermediate flowering, free-flowering all year; some heat tolerance; use in mixed containers, window boxes and the front of border plantings.
- *Time to initiate and develop roots.*—7–28 days.
- *Root description.*—Fibrous, fleshy, white.

Leaves:
- *Arrangement.*—Alternate, whorls.
- *Length.*—2.3–2.8 cm.
- *Width.*—1.9–2.4 cm.
- *Shape.*—Broadly elliptical.
- *Margin.*—Crenate, with ciliate (1) between each lobe.
- *Apex.*—Acute with 1 ciliate at the tip.
- *Base.*—Acuminate.
- *Color.*—Upper surface: RHS 137B. Lower surface: RHS 138B with varying amounts of anthocyanin in irregular blotches.
- *Texture.*—Glabrous.
- *Venation.*—Pinnate.
- *Venation color.*—RHS 144B fading into the leaf until almost disappearing.
- *Petioles.*—Length: 0.3–0.6 cm. Diameter: 0.1–0.15 cm. Color: RHS 144B. Texture: Glabrous.

Stems:
- *Length.*—10.0–12.0 cm.
- *Diameter.*—0.3 cm.

*Internode length.*—0.7–1.3 cm.
*Color.*—RHS 144B.
*Texture.*—Glabrous.
*Stem anthocyanin.*—Some present in irregular blotches.
*Pedicels.*—Length: 1.3–1.5 cm. Diameter: 0.1 cm. Color: RHS 144B. Texture: Glabrous.
*Peduncles.*—Length: 1.7–2.0 cm. Diameter: 0.15 cm. Color: RHS 144B. Texture: Glabrous.

Flower buds:
*Shape.*—Ovate.
*Length.*—0.6–0.8 cm.
*Diameter.*—0.5 cm.
*Color when first showing.*—RHS 47C.

Inflorescence:
*Blooming habit.*—Continuous and freely all through the year.
*Inflorescence type.*—Racemes in leaf axis and in leaf whorls.
*Number of flowers per raceme and/or whorl.*—10–15, including buds.
*Number of flowers per plant.*—50–75.
*Flower form.*—5 petals in a single whorl; 1 standard or dorsal (free); 2 lateral or lobed pairs (wing petals) deeply lobed.
*Lastingness of individual blooms.*—4–8 days.
*Fragrance.*—None.

Flowers:
*Immature flower.*—Color upper surface: Velvety, closest to RHS 45B. Length: 1.8–2.0 cm. Diameter: 1.9–2.1 cm.
*Mature flower.*—Color: Upper surface: All petals between RHS 45B and RHS 42A; lower lobes have an eyespot color of RHS 46A with a size of 0.2 cm. Lower surface: All petals RHS 42B. Diameter: 2.6–2.8 cm. Height: 2.8–3.0 cm.

Petals:
*Dorsal.*—Length: 0.9–1.1 cm. Width: 1.3–1.5 cm. Shape: Orbicular. Apex: Retuse.
*Lateral.*—Length: 1.4–1.7 cm. Width: 0.9–1.1 cm. Shape: Obovate. Apex: Retuse.
*Base.*—Fused.
*Petal margin.*—Entire.
*Petal texture.*—Papillose.

Sepals:
*Number.*—3; 1 larger than the others with a spur.
*Large sepal.*—Color: RHS N155D. Size: Length: 0.7 cm. Width: 0.6 cm. Shape: Ovate. Apex: Cuspidate. Base: Fused. Spur: Color: RHS 48D to RHS 48A at the tip. Length: 2.9–3.1 cm.
*Small sepals.*—Color: RHS 144C. Size: Length: 0.2 cm. Width: 0.1 cm. Shape: Ovate. Apex: Acute. Base: Fused.
*Sepal texture.*—Glabrous.

Reproductive organs:
*Stamens.*—5; more or less fused by the anthers and covering the ovary.
*Pollen cap color.*—RHS 45C.
*Pollen amount.*—Not observed.
*Pistil.*—1, complete.
*Fruit/seed set.*—Not observed.

Disease and insect resistance: Not observed.

COMPARISON WITH KNOWN CULTIVARS

'Fify Redtwo' differs from the female parent 'IMY-49-4' (unpatented) by having freer flowering, smaller flowers, and a more compact habit with smaller leaves than 'IMY-49-4'. 'Fify Redtwo' differs from the male parent 'IMY-54-2' (unpatented) by having smaller, red flowers and a more compact habit with smaller leaves than 'IMY-54-2'.

'Fify Redtwo' differs from the commercial cultivar 'Pixie Red' by having a larger flower, more vigor and freer flowering than 'Pixie Red'.

I claim:

1. A new and distinct cultivar of *impatiens* plant as shown and described herein.

* * * * *